US009254180B2

(12) United States Patent
Huitema et al.

(10) Patent No.: US 9,254,180 B2
(45) Date of Patent: Feb. 9, 2016

(54) SURGICAL INSTRUMENT WITH STAPLE REINFORCEMENT CLIP

(75) Inventors: Thomas W. Huitema, Cincinnati, OH (US); Jeffrey S. Swayze, Hamilton, OH (US); Julianne M. Siegel, Cincinnati, OH (US); Wendy A. Kerr, Cincinnati, OH (US); Steven G. Hall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 830 days.

(21) Appl. No.: 13/233,681

(22) Filed: Sep. 15, 2011

(65) Prior Publication Data

US 2013/0068821 A1 Mar. 21, 2013

(51) Int. Cl.
*A61B 17/068* (2006.01)
*A61B 17/064* (2006.01)
*A61B 19/00* (2006.01)
*A61B 17/072* (2006.01)
*A61B 17/122* (2006.01)

(52) U.S. Cl.
CPC ............ *A61B 19/40* (2013.01); *A61B 17/07292* (2013.01); *A61B 17/122* (2013.01); *A61B 19/00* (2013.01); *A61B 17/1227* (2013.01); *A61B 2019/4027* (2013.01)

(58) Field of Classification Search
CPC ........... A61B 17/07207; A61B 17/068; A61B 17/0644; A61B 17/064; A61B 17/0682; A61B 2017/00004; A61B 2014/0488; A61B 17/320092; A61B 17/0487; A61B 17/122
USPC ............ 227/175.1, 180.1, 901, 902; 606/219, 606/151
See application file for complete search history.

(56) References Cited

U.S. PATENT DOCUMENTS

| 2,303,131 | A | 11/1942 | Morgan |
| 3,364,200 | A | 1/1968 | Ashton et al. |
| 3,496,940 | A | 2/1970 | Steinman |
| 3,526,228 | A | 9/1970 | Lyng |
| 4,222,383 | A | 9/1980 | Schossow |
| 4,513,746 | A | 4/1985 | Aranyi et al. |

(Continued)

FOREIGN PATENT DOCUMENTS

| CA | 481943 | 2/1947 |
| DE | 199 24 311 | 11/2000 |

(Continued)

OTHER PUBLICATIONS

International Search Report dated Dec. 3, 2012 for Application No. PCT/US2012/054406.

(Continued)

*Primary Examiner* — Michelle Lopez
(74) *Attorney, Agent, or Firm* — Frost Brown Todd LLC

(57) ABSTRACT

An apparatus comprises a surgical instrument having a cutter and a stapler. The cutter is operable to sever a portion of tissue. The apparatus further comprises a plurality of staples where the stapler is operable to introduce the plurality of staples into tissue to form a staple line. The apparatus further comprises a reinforcement clip. The reinforcement clip is operable to be in selective communication with the staple line. The reinforcement clip comprises a crown, a leg portion, and a teeth portion. In some versions, the leg portion has a width operable to cover the area defined by the staple line. In some versions, the teeth portion is configured to anchor into tissue.

20 Claims, 13 Drawing Sheets

(56) References Cited

U.S. PATENT DOCUMENTS

| | | |
|---|---|---|
| 4,549,545 A | 10/1985 | Levy |
| 4,610,250 A | 9/1986 | Green |
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,217,473 A | 6/1993 | Yoon |
| 5,234,449 A * | 8/1993 | Bruker et al. ............... 606/158 |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,411,193 A | 5/1995 | Culp |
| 5,415,334 A | 5/1995 | Williamson, IV et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Shimizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,855 A | 9/1998 | Rayburn et al. |
| 5,814,055 A | 9/1998 | Knodel et al. |
| 5,814,057 A | 9/1998 | Oi et al. |
| 5,833,695 A | 11/1998 | Yoon |
| 5,843,096 A | 12/1998 | Igaki et al. |
| 5,902,312 A | 5/1999 | Frater et al. |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,721,930 B2 | 5/2010 | McKenna et al. |
| 7,738,971 B2 | 6/2010 | Swayze et al. |
| 7,744,624 B2 * | 6/2010 | Bettuchi ............... 606/207 |
| 7,845,533 B2 | 12/2010 | Marczyk et al. |
| 2002/0165559 A1 | 11/2002 | Grant et al. |
| 2003/0120284 A1 | 6/2003 | Palacios et al. |
| 2003/0183671 A1 | 10/2003 | Mooradian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0149069 A1 * | 7/2005 | Bertolero et al. ............ 606/151 |
| 2005/0154403 A1 | 7/2005 | Sauer et al. |
| 2005/0245965 A1 | 11/2005 | Orban, III et al. |
| 2005/0249772 A1 | 11/2005 | Malaviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0112360 A1 | 5/2007 | De Deyne et al. |
| 2007/0118163 A1 * | 5/2007 | Boudreaux et al. ............ 606/157 |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |
| 2008/0078800 A1 | 4/2008 | Hess et al. |
| 2008/0078801 A1 | 4/2008 | Shelton, IV et al. |
| 2008/0078802 A1 | 4/2008 | Hess et al. |
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |

(56) References Cited

U.S. PATENT DOCUMENTS

| | | | |
|---|---|---|---|
| 2008/0110959 A1 | 5/2008 | Orban, III et al. |
| 2008/0114381 A1 | 5/2008 | Voegele et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0012545 A1 | 1/2009 | Williamson et al. |
| 2009/0076510 A1 | 3/2009 | Bell et al. |
| 2009/0118747 A1 | 5/2009 | Bettuchi et al. |
| 2009/0318937 A1* | 12/2009 | Matsuoka et al. ............ 606/151 |

FOREIGN PATENT DOCUMENTS

| | | |
|---|---|---|
| EP | 328 401 | 8/1989 |
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| GB | 1 151 993 | 5/1969 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2789885.
Abstract for FR2850281.
Abstract for JP1072740.
Abstract for JP11309151.
Abstract for JP3146773.
Abstract for JP5076586.

* cited by examiner

SURGICAL INSTRUMENT WITH STAPLE REINFORCEMENT CLIP

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
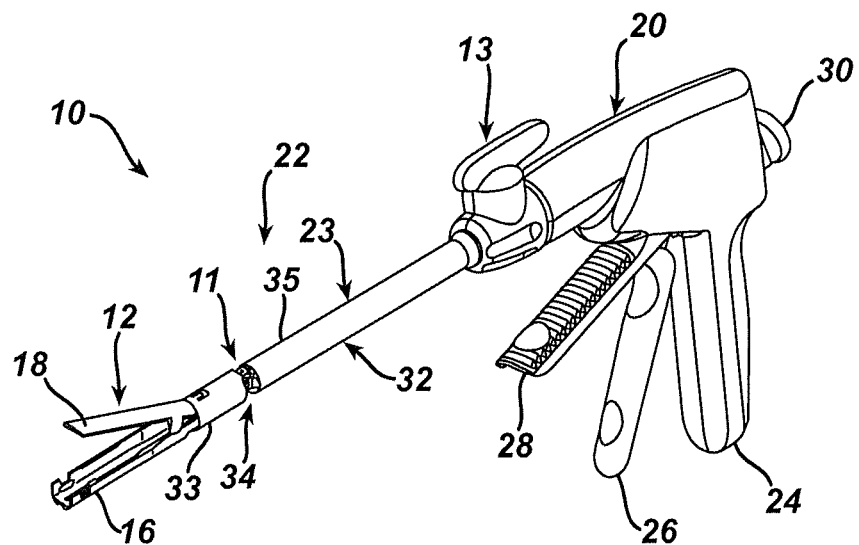
FIG. 1A depicts a perspective view of an articulating surgical instrument with an end effector in a nonarticulated position.
Figure 1B:
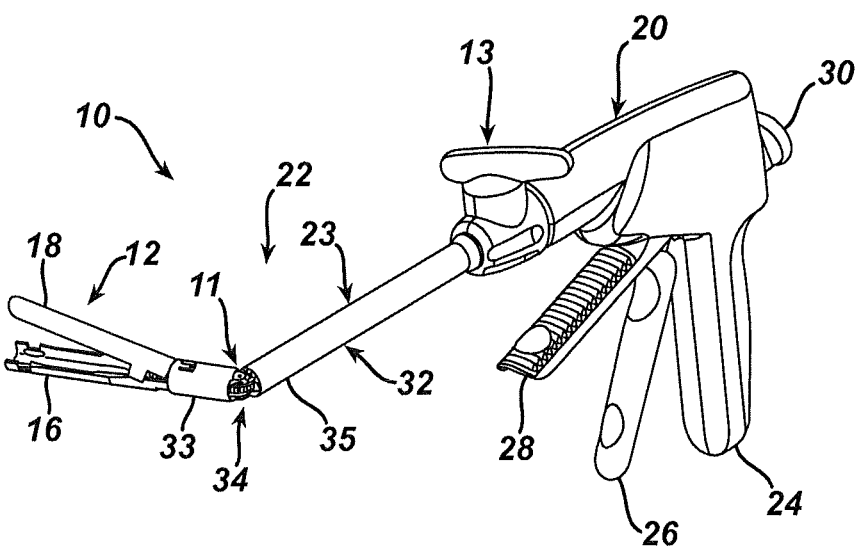
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical stapling and severing instrument (10) includes handle portion (20) connected to implement portion (22), the latter further comprising shaft (23) distally terminating in an articulation mechanism (11) and a distally attached end effector (12). Once articulation mechanism (11) and end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal closure ring (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
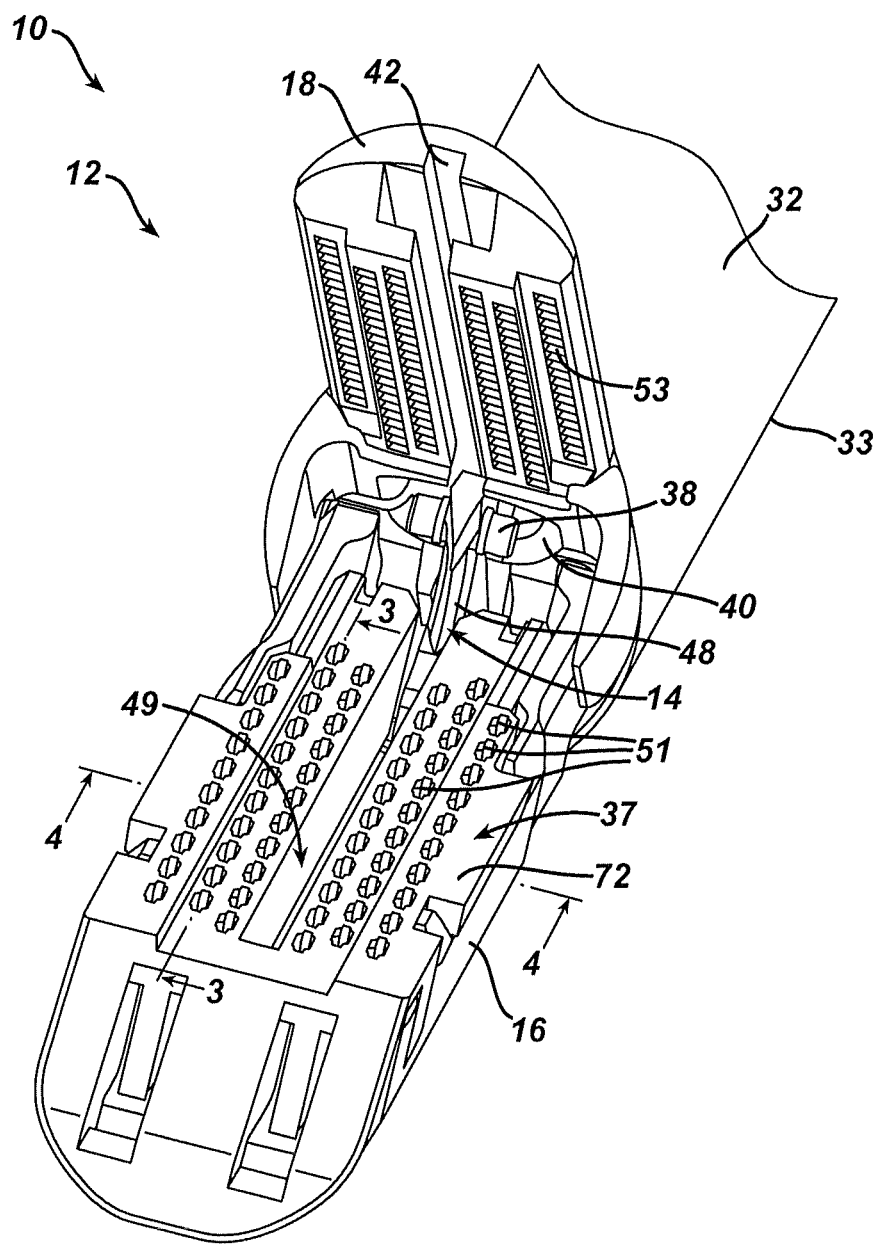
FIG. 2 depicts a perspective view of an opened end effector of the surgical instrument of FIGS. 1A-1B.
Figure 3A:
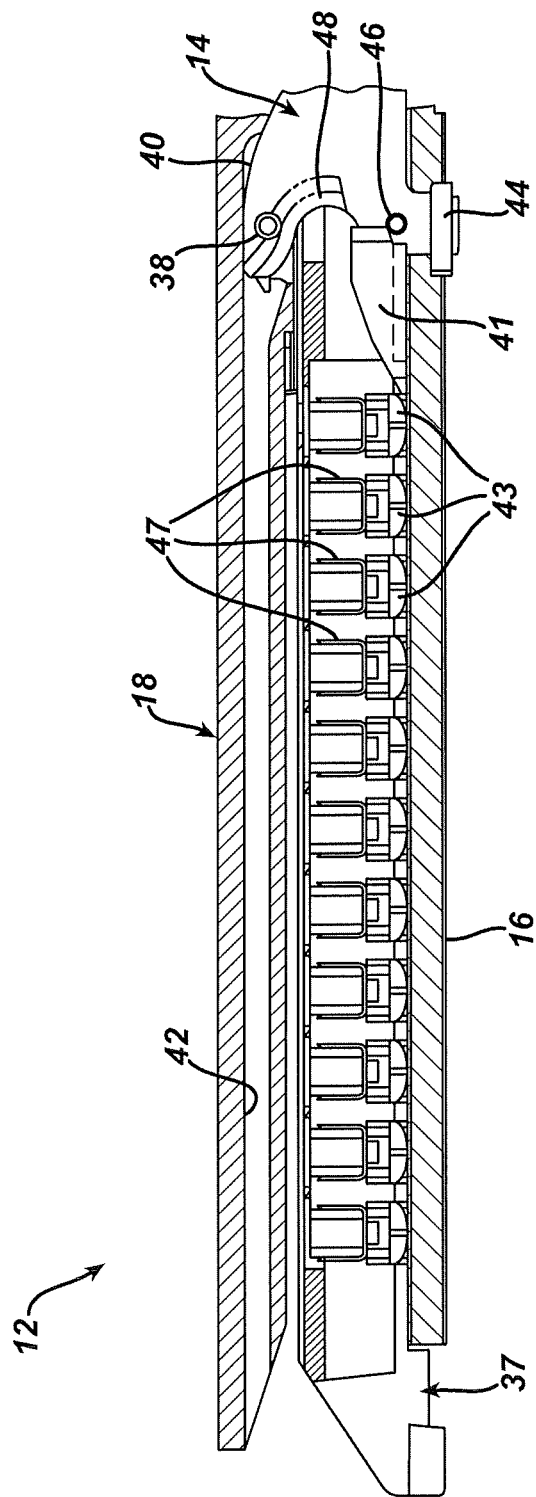
FIG. 3A depicts a side cross-sectional view of the end effector of FIG. 2, taken along line 3-3 of FIG. 2, with the firing bar in a proximal position.
Figure 3B:
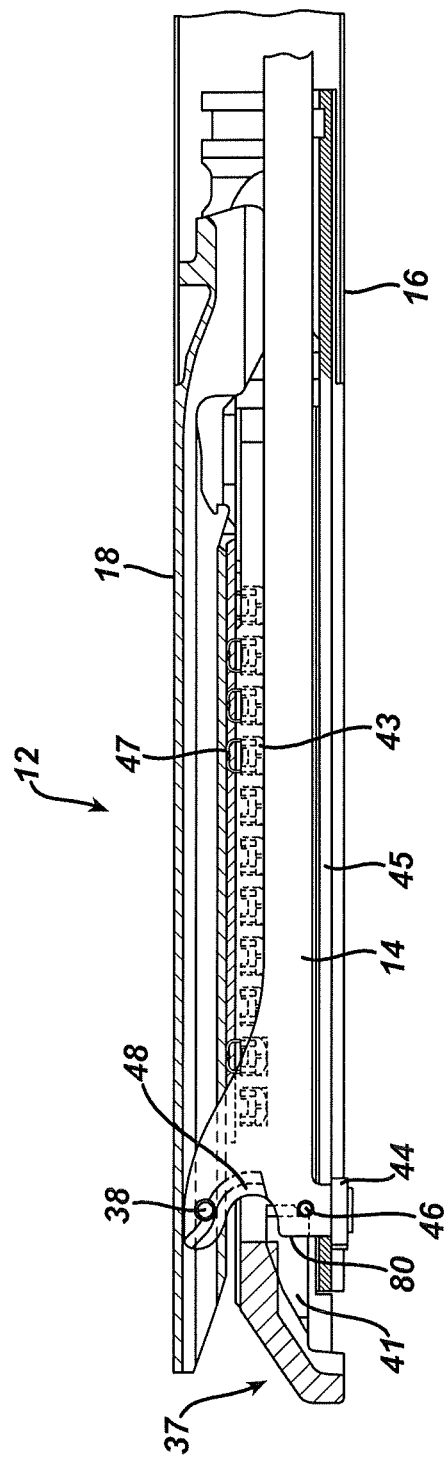
FIG. 3B depicts a side cross-sectional view of the end effector of FIG. 2, taken along line 3-3 of FIG. 2, but showing the firing bar in a distal position.
Figure 4:
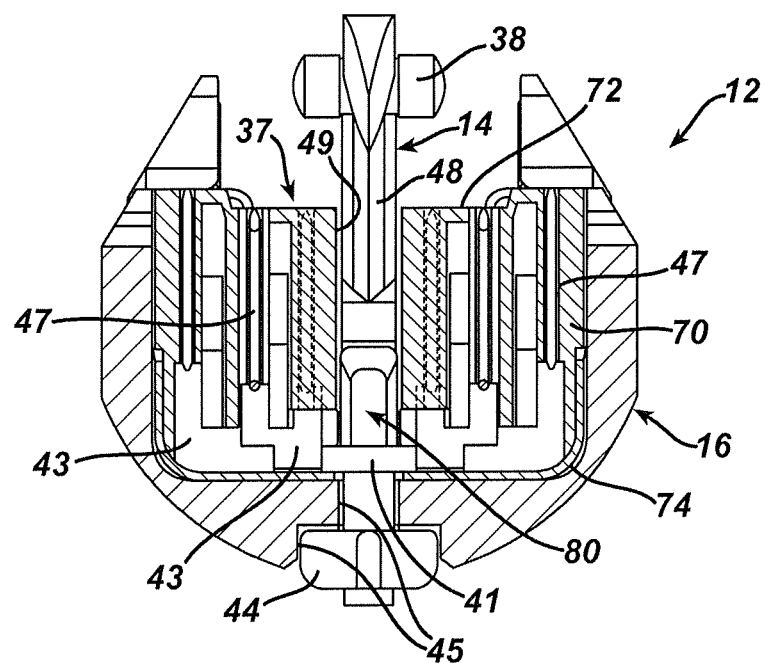
FIG. 4 depicts an end cross-sectional view of the end effector of FIG. 2, taken along line 4-4 of FIG. 2.
Figure 5:
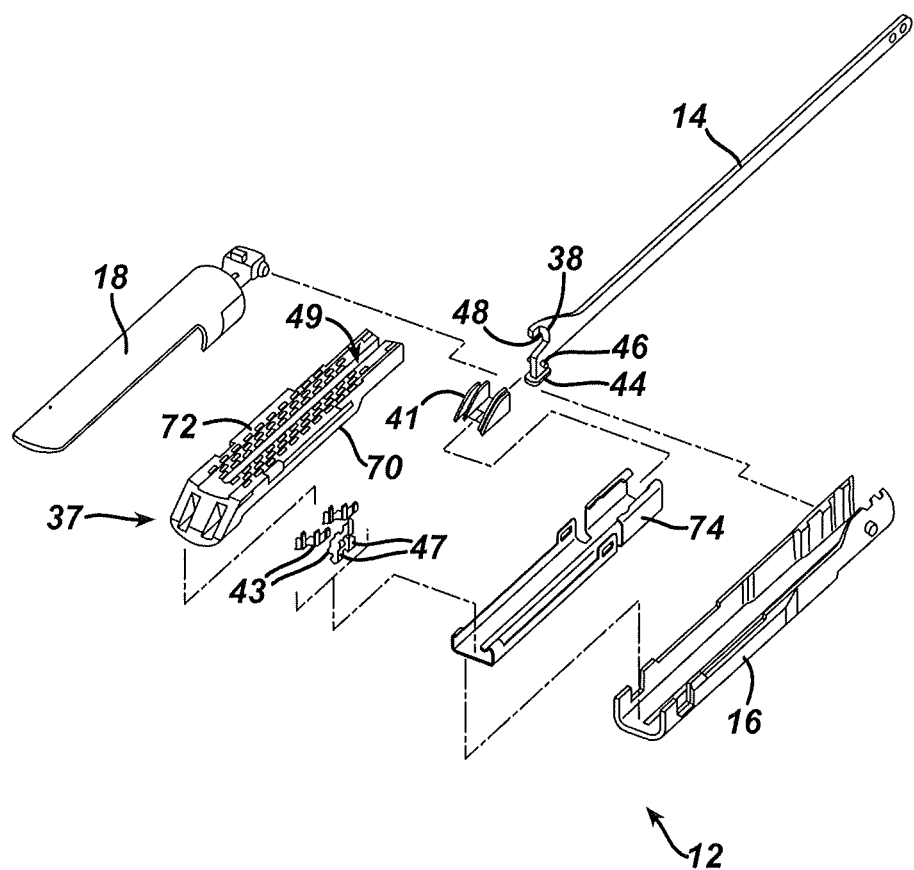
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through distal part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into slot (49) within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
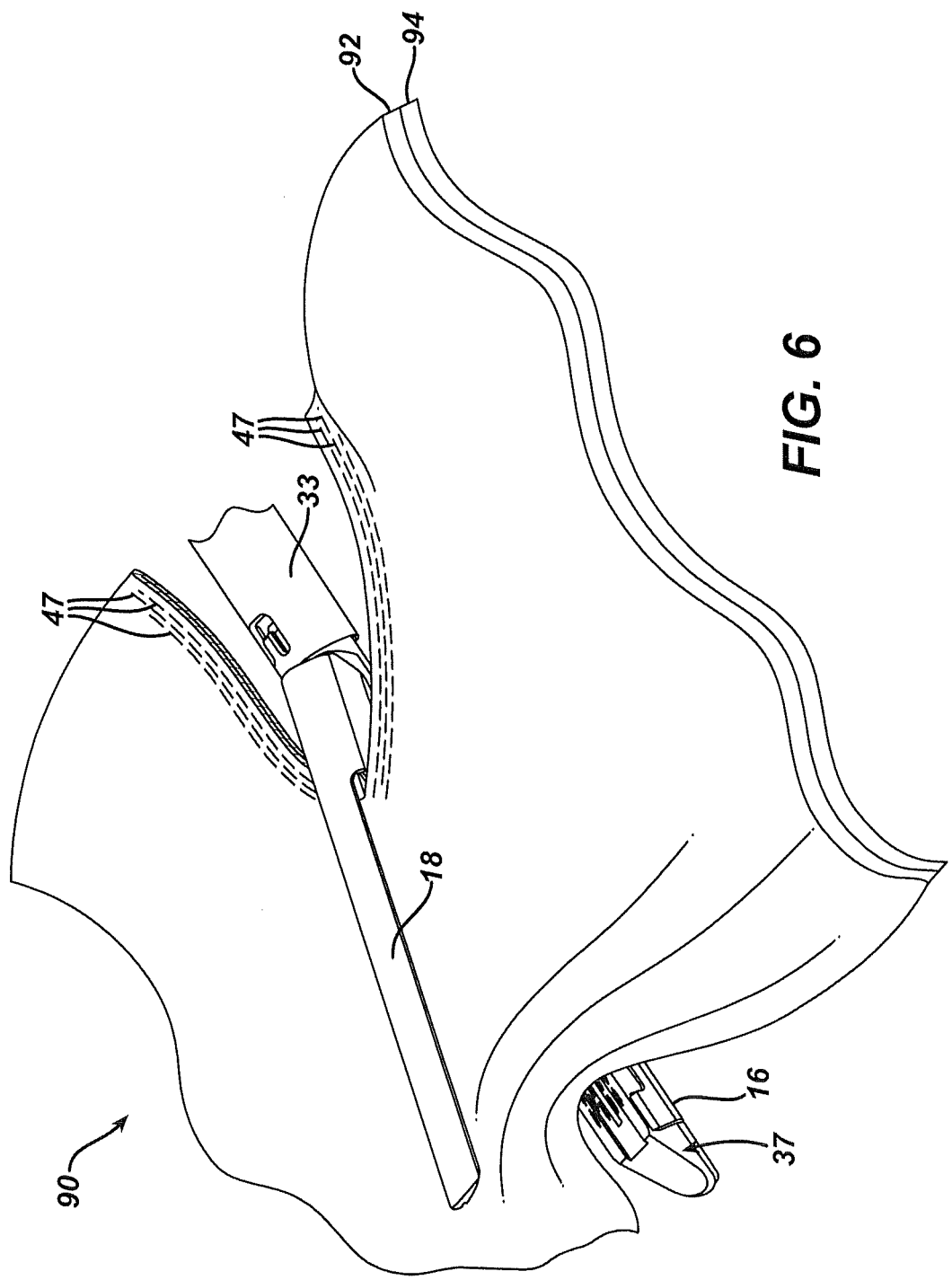
FIG. 6 depicts a perspective view of the end effector of FIG. 2, positioned at tissue and having been actuated once in the tissue.

FIG. 6 shows end effector (12) having been actuated through a single stroke through tissue (90). Cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930.

As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Resilient Staple Reinforcement Clip

Figure 7:
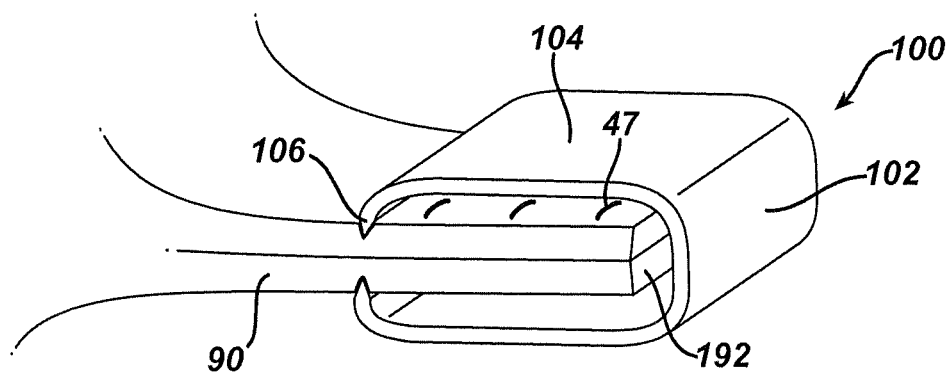
FIG. 7 depicts a perspective view of an exemplary reinforcement clip having a resilient structure.

FIG. 7 shows an exemplary reinforcement clip (100). It will be appreciated that once staples (47) are inserted into the surgical site, reinforcement clip (100) may be applied along severed tissue (192) adjacent to the implanted staples (47) to reinforce the tissue seal provided by staples (47). However, it will be appreciated that reinforcement clip (100) may be used in various other ways as would be apparent to one of ordinary skill in the art in view of the teachings herein.

Reinforcement clip (100) comprises a crown (102), leg portion (104) and teeth (106). In the present example, reinforcement clip (100) has a rounded rectangular cross section. In other merely exemplary versions, reinforcement clip (100) may have a c-shaped cross section. Other suitable shapes for reinforcement clip (100) may be used as would be apparent to one of ordinary skill in the art in view of the teachings herein. As seen in the illustrated version of FIG. 7, leg portion (104) is long enough to cover staples (47) and portion of tissue (90) that is affected by a surgical procedure. For instance, during a surgical procedure, the user may use instrument (10) to apply staples (47) to tissue (90) adjacent to the edges of tissue (192) severed by instrument (10). Once staples (47) are placed in tissue (90), the user may then apply reinforcement clip (100) to further secure the tissue coupling provided by staples (47). Reinforcement clip (100) could be fed through a separate trocar such that two trocars would ultimately be used in the procedure—one trocar for inserting instrument (10) to staple a portion of tissue (90) and another trocar for inserting graspers or any suitable instrument for holding and applying reinforcement clip (100). In the alternative, instrument (10) and reinforcement clip (100) may be inserted through a single large trocar wide enough to fit reinforcement clip (100) and instrument (10). Other suitable ways of positioning reinforcement clip (100) and instrument (10) at the surgical site will be apparent to those of ordinary skill in the art in view of the teachings herein.

In the present example, reinforcement clip (100) has a width that extends approximately along the portion of tissue (90) where staples (47) are applied along severed tissue (192). In other exemplary versions, reinforcement clip (100) may have a width significantly wider than tissue (90) where staples (47) are inserted. Of course, any suitable size or width for reinforcement clip (100) may be used as would be apparent to one of ordinary skill in the art in view of the teachings herein.

Reinforcement clip (100) of the present example comprises a dissolvable material such as, for example, polydioxanone (PDS) such that once reinforcement clip (100) is applied, it dissolves over time without requiring the user to remove reinforcement clip (100). Other suitable materials may be used for reinforcement clip such as polycaprolactone (PCL), polyglycolide (PGA), polylactic acid (PLA), polylactic-co-glycolic acid (PLLA), or any other suitable material as would be apparent to one of ordinary skill in the art in view of the teachings herein. It should also be understood that reinforcement clip (100) may be removable after implanting reinforcement clip (100) within a patient. Furthermore, in will be appreciated that reinforcement clip (100) may be constructed out of any suitable material as would be apparent to one of ordinary skill in the art in view of the teachings herein. In the present example, reinforcement clip (100) is constructed of a resilient material such that reinforcement clip (100) is biased to hold the position shown generally in FIGS. 7-8. As such, the user may use graspers or any other suitable instruments to spread and release leg portions (104) and thereby allow reinforcement clip (100) to close upon tissue (90). In other exemplary versions, reinforcement clip (100) may be slid over the surgical site by sliding reinforcement clip in a direction parallel to severed tissue edges (192).

Crown (102) is operable to keep leg portion (104) sufficiently clamped with sufficient pressure such that leg portion (104) in conjunction with teeth (106) are operable to close around tissue (90) adjacent to where staples (47) are applied. In other exemplary versions, however, crown (102) may comprise a living hinge or any other suitable structure, which will be described in further detail below. In the present example, crown (102) comprises a resilient material. In other exemplary versions, any suitable structure for crown (102) may be used as would be apparent to one of ordinary skill in the art in view of the teachings herein.

Figure 8:
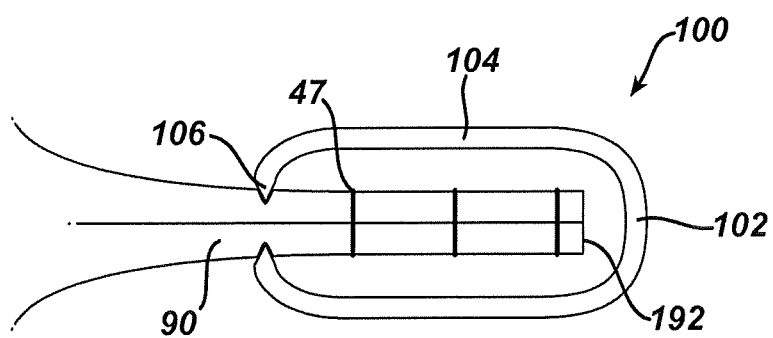
FIG. 8 depicts a side view of the reinforcement clip of FIG. 7.

Teeth (106) are shaped to have a blunt edge that presses against tissue (90) as shown in FIG. 7, without necessarily piercing or penetrating tissue (90). In some versions, teeth (106) may be coated with a therapeutic material (e.g., a coagulant, etc.). As seen in FIGS. 7-8, teeth (106) are pressed against the surface of tissue (90) to secure reinforcement clip (100) around tissue (90). In other merely exemplary versions, teeth (106) may comprise a sharp tip such that teeth (106) are anchored within tissue (90). As seen in the illustrated version, as teeth (106) are squeezed together, teeth (106) apply opposing pressure against tissue (90). It will be appreciated that as a result of this opposing pressure, the portion of tissue (90) clamped within reinforcement clip (100) may be substantially isolated from opposing forces that might otherwise tend to separate the layers of tissue (90) from each other. As a result, staples (47) may be less likely to tear tissue (90) within reinforcement clip (100). It should also be understood that clamping forces provided by teeth (106) may assist in providing hemostasis at staples (470) and at severed edges (192).

III. Exemplary Malleable Staple Reinforcement Clip

Figure 9A:
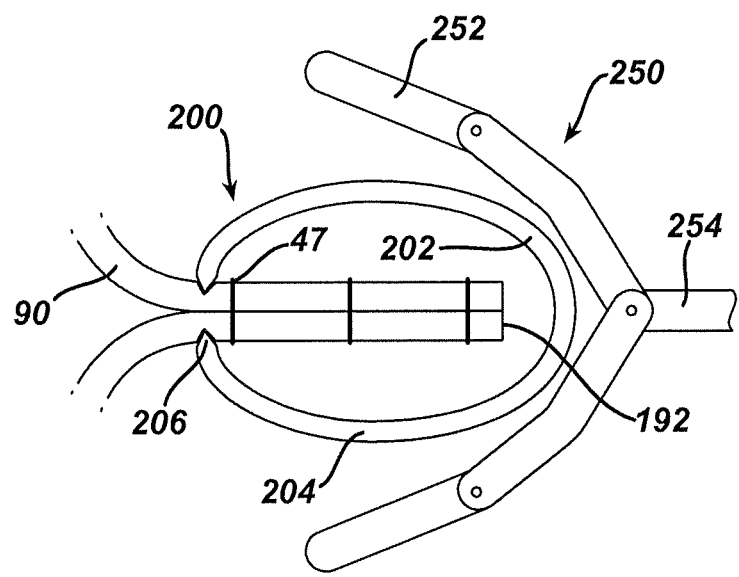
FIG. 9A depicts a side view of an exemplary alternative reinforcement clip having a malleable structure with an applier.
Figure 9B:
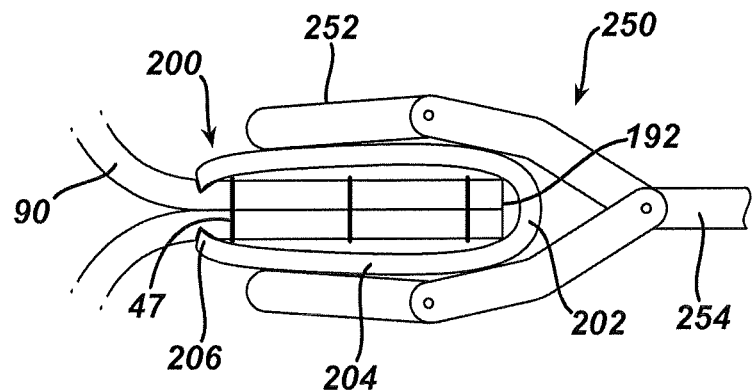
FIG. 9B depicts a side view of the reinforcement clip of FIG. 9A with the applier collapsing the reinforcement clip.

FIGS. 9A-B show an exemplary reinforcement clip (200) having malleable properties, as reinforcement clip (200) is applied to tissue (90). FIG. 9A shows tissue (90) having been already stapled and severed leaving a severed edge (192). Reinforcement clip (200) is being placed over tissue (90) in FIG. 9A such that leg portion (204) covers staples (47). Reinforcement clip (200) further comprises crown (202) and teeth (206). Reinforcement clip (200) is malleable such that an applier (250) having jaws (252) connected to shaft (254) may be used to collapse reinforcement clip (200) around staples (47) where tissue (90) has been severed and stapled.

FIG. 9B shows jaws (252) closed around reinforcement clip (200) causing reinforcement clip (200) to collapse around staples (47) and severed tissue (192). Once collapsed, reinforcement clip (200) is operable to retain its collapsed shape such that applier (250) may be removed while leaving reinforcement clip (200) clamped around the surgical area.

IV. Exemplary Flexible Staple Reinforcement Clip

Figure 10A:
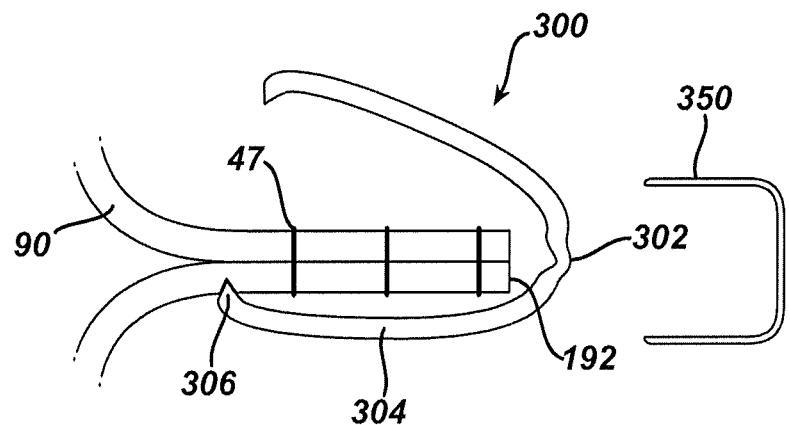
FIG. 10A depicts a side view of an exemplary alternative reinforcement clip having a flexible structure with a locking clip.
Figure 10B:
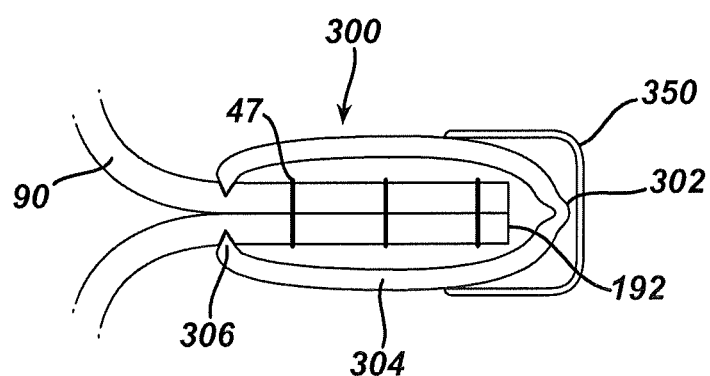
FIG. 10B depicts a side view of the reinforcement clip of FIG. 10A with the locking clip applied to the clip.

FIGS. 10A-B show an exemplary reinforcement clip (300) having a generally flexible feature that is not biased to hold any particular position. In particular, reinforcement clip (300) of this example comprises a living hinge (302) that connects leg portions (304). Leg portions (304) lead to teeth (306). The illustrated version also shows a locking feature (350) that may be used to close reinforcement clip (300) around tissue (90). Living hinge (302) is sufficiently flexible so as to allow leg portions (304) to be easily separated to positions on top of staples (47). After reinforcement clip (300) has been sufficiently placed around staples (47), lock feature (350) may be slid onto reinforcement clip (300) as shown in FIG. 10B, thereby causing reinforcement clip (300) to be locked in a clamped position. In the present example, locking feature (350) is positioned on living hinge (302), but any suitable location for locking feature (350) may be used as would be apparent to one of ordinary skill in the art in view of the teachings herein. For example, locking feature (350) may be clasped around leg portion (304). In the present example, locking feature (350) comprises a U-shaped clip, but any suitable structure for locking feature may be used. In some merely exemplary versions, locking feature (350) may comprise a barb, a clasp, or any other suitable locking mechanism as would be apparent to once of ordinary skill in the art in view of the teachings herein.

Figure 11:
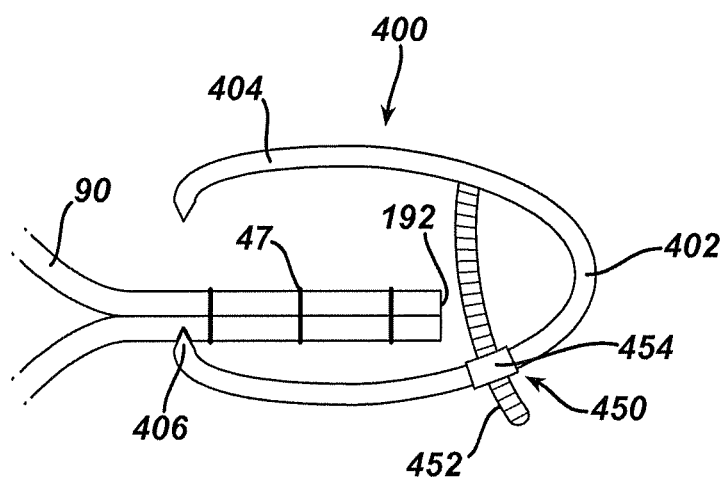
FIG. 11 depicts a side view of an exemplary alternative reinforcement clip with a ratcheting feature.

FIG. 11 shows one merely illustrative alternative form that locking feature (350) may take. In particular, FIG. 11 shows a reinforcement clip (400) that includes an integral ratcheting feature (450). Reinforcement clip (400) also includes a leg portion (404), a crown (402), and teeth (406). Ratcheting feature (450) comprises an adjustment strap (452) that passes through a one way gate (454). Gate (454) is positioned on one leg portion (404) while adjustment strap (452) extends from the other leg portion (404). As adjustment strap (452) is pulled through gate (454), reinforcement clip (400) is closed tighter and prevents strap (452) from being reversed through gate (454). Strap (452) and gate (454) thus operate similar to a conventional zip tie, cable tie, or tie-wrap. By controlling the length of adjustment strap (452) that is ultimately pulled through gate (454), the user can control the tightness of reinforcement clip (400) and thus adjust the tightness of reinforcement clip (400) based on the thickness of tissue (90) at the surgical site.

Figure 13:
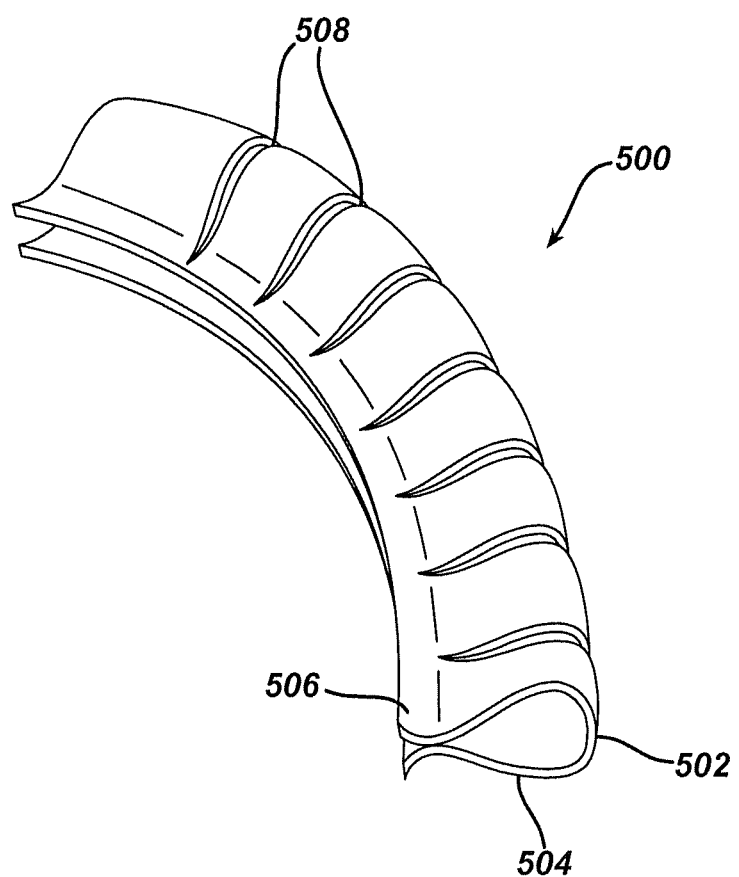
FIG. 13 depicts a perspective view of an exemplary alternative reinforcement clip having a partially segmented structure.

FIG. 13 shows yet another merely exemplary version of a reinforcement clip (500). Reinforcement clip (500) of this example has a partially segmented structure. Reinforcement clip (500) includes a leg portion (504), a crown (502), and a clamping region (506). Reinforcement clip (500) further comprises a plurality of transversely formed notches (508) spaced apart along the length of reinforcement clip (500). In the present example, notches (508) are spaced apart evenly along reinforcement clip (500), but any suitable spacing configuration may be used as would be apparent to one of ordinary skill in the art in view of the teachings herein. For example, notches (508) may be concentrated in one region of reinforcement clip (500) and sparser in others. It will be appreciated that notches (508) are operable to provide flexing of reinforcement clip (500) in a manner that follows the motion and/or contours of any tissue (90) enclosed by reinforcement clip (500). It will further be appreciated that reinforcement clip (500) may be operable to provide relief in the event that fluid pressure builds up between reinforcement clip (500) and tissue (90) being held by reinforcement clip (90). Other suitable ways in which segmentation may be provided in a reinforcement clip will be apparent to those of ordinary skill in the art in view of the teachings herein.

Figure 12:
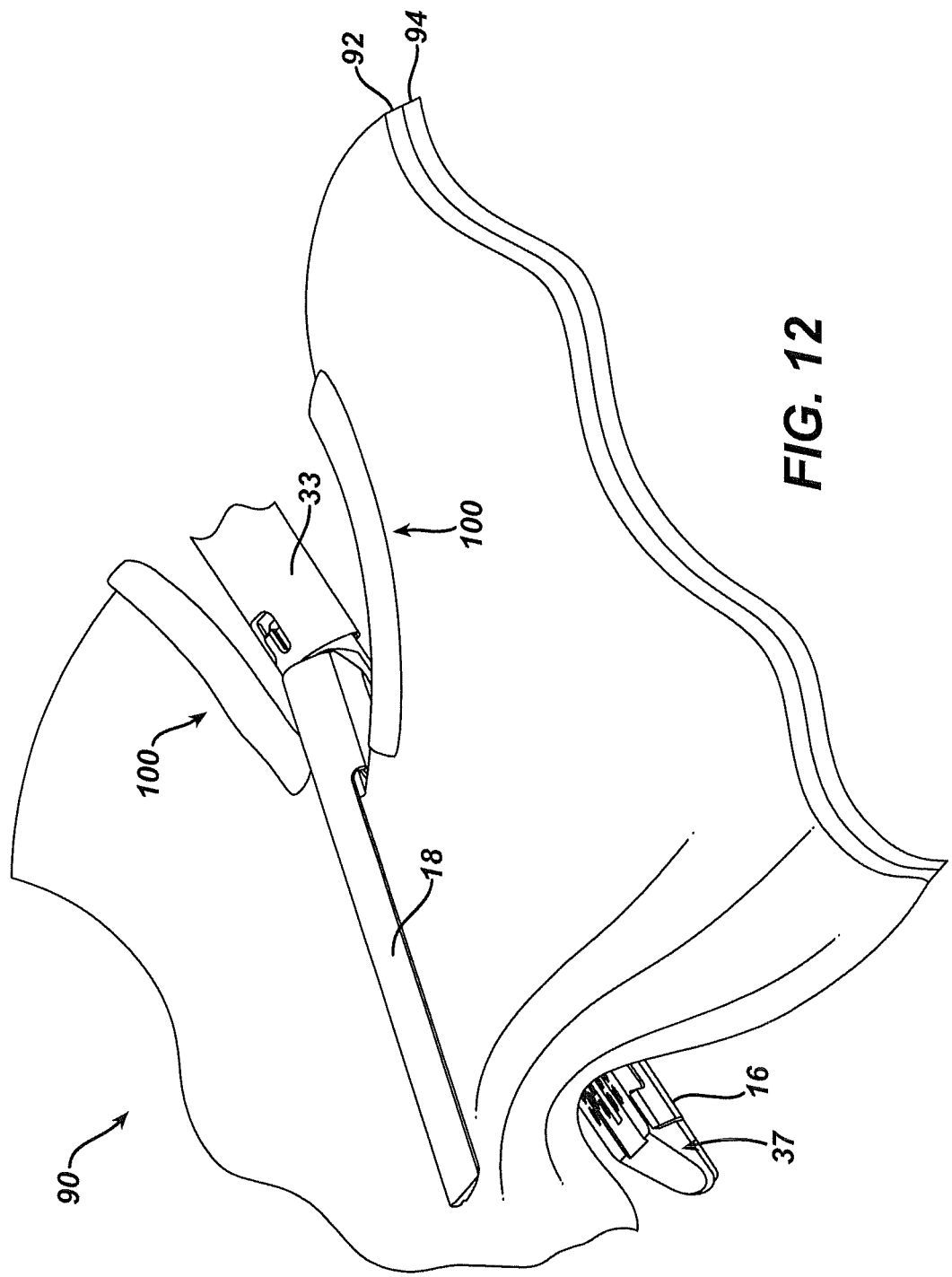
FIG. 12 depicts a perspective view of a reinforcement clip with an end effector where the reinforcement clip has been applied to tissue.

FIG. 12 shows reinforcement clip (100) having been used within tissue (90) to secure a staple line (covered by reinforcement clip (100)). As mentioned above, over time, reinforcement clip (100) may gradually dissolve, or in other exemplary versions reinforcement clip (100) may be removed by the user. In other alternative versions, reinforcement clip (100) may simply remain within the patient without being removed or dissolved. The other clips (200, 300, 400, 500) described herein may also be used as shown in FIG. 12.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
    (a) a surgical instrument comprising a cutter and a stapler, wherein the cutter is configured to sever a portion of tissue;
    (b) a plurality of staples in communication with the stapler, wherein the stapler is configured to introduce the plurality of staples to a severed portion of tissue, wherein the stapler is configured to form a staple line with the plurality of staples; and
    (c) a reinforcement clip configured to selectively cover the staple line, wherein the reinforcement clip is configured to be applied after the plurality of staples have been introduced to a portion of severed tissue, wherein the reinforcement clip comprises:
        (i) a crown portion, wherein the crown portion has a pair of opposing ends,
        (ii) a leg portion extending transversely relative to the crown portion, wherein the leg portion comprises opposing, continuous legs, wherein the legs together define a first gap between each leg at each end of the crown portion, and
        (iii) teeth portions extending transversely relative to each leg, wherein the teeth portions define a second gap between the teeth portions such that the teeth portions are separated from each other by the second gap,
    wherein the leg portion has a width operable to cover an area defined by the staple line, wherein the teeth portion is configured to anchor the teeth portion into tissue, wherein the reinforcement clip is configured to cover the staple line and the portion of severed tissue; wherein the leg portion further comprises a pair of opposing legs, wherein the crown portion is positioned between the opposing legs and is configured such that the legs cooperate to compress apposed layers of tissue against each other, wherein the reinforcement clip is configured to only partially envelop tissue;
    wherein the clip comprises a plurality of transversely formed notches spaced apart along the length thereof, wherein each of the notches extends along a portion of each of the legs and the crown.

2. The apparatus of claim 1, wherein the crown portion comprises a living hinge.

3. The apparatus of claim 2, wherein the crown portion further comprises at least one locking feature operable to lock the living hinge, thereby fixing the living hinge in a predetermined position.

4. The apparatus of claim 3, wherein the at least one locking feature comprises at least one clasp.

5. The apparatus of claim 2, wherein the living hinge comprises a ratcheting feature, wherein the ratcheting feature is configured such that the living hinge is moveable in only one direction.

6. The apparatus of claim 1, wherein the reinforcement clip comprises an absorptive material.

7. The apparatus of claim 6, wherein the absorptive material comprises polydioxanone.

8. The apparatus of claim 1, wherein the reinforcement clip is configured to form a seal around a severed portion of tissue.

9. The apparatus of claim 1, wherein the reinforcement clip comprises an elongated C-shaped cross section.

10. The apparatus of claim 1, wherein the reinforcement clip comprises a deformable material.

11. The apparatus of claim 1, wherein the surgical instrument is configured to be actuated to introduce the staples using the stapler into a portion of tissue, wherein the reinforcement clip is configured to cover all of the staples introduced in a single actuation.

12. The apparatus of claim 1, further comprising an applier instrument, wherein the applier instrument is configured to clamp the reinforcement clip over the staple line.

13. The apparatus of claim 12, wherein the applier instrument is further configured to clamp with sufficient force so as to squeeze and secure the staple line.

14. The apparatus of claim 1, wherein the reinforcement clip comprises an inner portion and an outer portion, wherein the inner portion is positionable around a portion of severed tissue, wherein the teeth portion of the reinforcement clip is configured to clamp with sufficient force such that the inner portion remains mechanically isolated from the outer portion.

15. The apparatus of claim 1, wherein the reinforcement clip is configured to enclose the staple line without contacting the staple line.

16. An apparatus comprising:
(a) a surgical instrument comprising a cutter and a stapler, wherein the cutter is configured to sever a portion of tissue;
(b) a plurality of staples in communication with the stapler, wherein the stapler is configured to introduce the plurality of staples to a severed portion of tissue, wherein the stapler is configured to form a staple line with the plurality of staples;
(c) a clip comprising:
   (i) a crown extending along an axis, wherein the crown has a pair of opposing ends,
   (ii) a pair of opposing, continuous legs extending transversely relative to the axis with a gap between each of the legs on each end of the crown, wherein the crown and the legs form a generally C-shaped portion, in cross-section along a plane that is perpendicular to the axis, of the clip, and
   (iii) teeth positioned at the end of each of the opposing legs, wherein the teeth extend transversely from a respective opposing leg of the C-shaped portion and are oriented towards each other,
   wherein the clip is configured to enclose a staple line, wherein the legs of the clip comprise a width sufficiently wide to overlay the width of the staple line, wherein the teeth are configured to anchor opposing portions of apposed layers of tissue, wherein the reinforcement clip is configured to only partially envelop tissue, wherein the crown comprises a deformable material;
   wherein the clip comprises a plurality of transversely formed notches spaced apart along the length thereof, wherein each of the notches extends along a portion of each of the continuous legs and the crown; and
(d) a surgical applier, wherein the applier is in selective communication with the clip, wherein the applier is configured to deliver the clip to a surgical site, wherein the applier is further configured to clamp the clip, thereby anchoring the clip, wherein the applier is further configured to clamp the clip over the staple line.

17. The apparatus of claim 16, wherein the crown comprises a living hinge and a locking feature, wherein the living hinge is operable to enable the legs to be moveable, wherein the locking feature is configured to selectively prevent the living hinge from moving.

18. The apparatus of claim 17, wherein the locking feature comprises a barb positionable over the living hinge.

19. The apparatus of claim 16, wherein the clip comprises an absorptive material configured to be absorbed over time.

20. An apparatus comprising:
(a) a clip comprising:
   (i) a crown, wherein the crown has a pair of opposing ends,
   (ii) opposing, first and second continuous legs extending transversely relative to the crown with a gap between the legs on each end of the crown, and
   (iii) a clamping region, wherein the legs of the clip comprise a width sufficiently wide to overlay the width of the staple line,
   wherein the clip is configured to only partially envelop tissue, wherein the clamping region is configured to anchor tissue, wherein the crown comprises a deformable material, wherein the clip comprises a plurality of transversely formed notches spaced apart along the length thereof, wherein each of the notches extends along a portion of the first continuous leg, the crown, and a portion of the second continuous leg; and
(b) a surgical applier, wherein the applier is in selective communication with the clip, wherein the applier is configured to deliver the clip to a surgical site, wherein the applier is further configured to clamp the clip, thereby anchoring the clip, wherein the applier is further configured to clamp the clip over a staple line.

* * * * *